United States Patent
Wu et al.

(10) Patent No.: US 10,111,994 B2
(45) Date of Patent: Oct. 30, 2018

(54) BLOOD PUMP WITH SEPARATE MIXED-FLOW AND AXIAL-FLOW IMPELLER STAGES AND MULTI-STAGE STATORS

(71) Applicant: HeartWare, Inc., Miami Lakes, FL (US)

(72) Inventors: Jingchun Wu, Irvine, CA (US); Michael Ricci, Camarillo, CA (US); David Paden, Goleta, CA (US); Shaun Snyder, Santa Barbara, CA (US)

(73) Assignee: HeartWare, Inc., Miami Lakes, FL (US)

( * ) Notice: Subject to any disclaimer, the term of this patent is extended or adjusted under 35 U.S.C. 154(b) by 682 days.

(21) Appl. No.: 14/277,378

(22) Filed: May 14, 2014

(65) Prior Publication Data

US 2014/0341726 A1 Nov. 20, 2014

Related U.S. Application Data (60) Provisional application No. 61/823,224, filed on May 14, 2013.

(51) Int. Cl.
*A61M 1/10* (2006.01)
*F04D 1/02* (2006.01)
(Continued)

(52) U.S. Cl.
CPC .............. *A61M 1/101* (2013.01); *F04D 1/025* (2013.01); *F04D 1/04* (2013.01); *F04D 3/00* (2013.01);
(Continued)

(58) Field of Classification Search
CPC .......... A61M 1/101; F04D 1/025; F04D 1/04; F04D 3/00
(Continued)

(56) References Cited

U.S. PATENT DOCUMENTS

| | | | | |
|---|---|---|---|---|
| 4,625,712 A | * | 12/1986 | Wampler | A61M 1/102 128/DIG. 3 |
| 4,846,152 A | | 7/1989 | Wampler et al. | |
| 4,850,796 A | | 7/1989 | Miller | |
| 4,944,722 A | | 7/1990 | Carriker et al. | |
| 5,112,200 A | * | 5/1992 | Isaacson | F04D 13/0646 415/900 |
| 5,211,546 A | * | 5/1993 | Isaacson | F04D 13/0646 415/900 |

(Continued)

FOREIGN PATENT DOCUMENTS

| | | | | |
|---|---|---|---|---|
| CA | 2374656 A1 | * | 12/2000 | ............ F16C 32/047 |
| CA | 2377934 A1 | * | 1/2001 | ............. F04D 3/005 |

(Continued)

OTHER PUBLICATIONS

PCT International Search Report for International Patent Application No. PCT/US2011/056646, dated Jan. 27, 2012 (5 pages).

(Continued)

*Primary Examiner* — Jason Newton
(74) *Attorney, Agent, or Firm* — Christopher & Weisberg, P.A.

(57) ABSTRACT

A pump for a fluid which can be blood has a stator housing and a rotor hub with leading and trailing portions and an intermediate portion disposed therebetween. At least one impeller blade at the leading portion drives circumferential and axial components of a flow into a pump annulus or intermediate pathway portion. At least one stator blade extends radially inward from the stator housing within the intermediate pathway portion and is configured to reduce a circumferential component of the flow.

20 Claims, 6 Drawing Sheets

(51) Int. Cl.
  *F04D 1/04*   (2006.01)
  *F04D 3/00*   (2006.01)
  *A61M 1/12*   (2006.01)

(52) U.S. Cl.
  CPC ........... *A61M 1/1012* (2014.02); *A61M 1/122* (2014.02); *A61M 1/125* (2014.02)

(58) Field of Classification Search
  USPC ...................................................... 415/209.1
  See application file for complete search history.

(56) References Cited

U.S. PATENT DOCUMENTS

| | | | |
|---|---|---|---|
| 5,376,114 A | 12/1994 | Jarvik | |
| 5,678,306 A | 10/1997 | Bozeman, Jr. et al. | |
| 5,692,882 A * | 12/1997 | Bozeman, Jr. | A61M 1/10 310/216.013 |
| 5,695,471 A | 12/1997 | Wampler | |
| 5,755,784 A | 5/1998 | Jarvik | |
| 5,762,599 A * | 6/1998 | Sohn | A61F 2/0018 417/420 |
| 5,776,190 A | 7/1998 | Jarvik | |
| 5,824,070 A | 10/1998 | Jarvik | |
| 5,851,174 A | 12/1998 | Jarvik et al. | |
| 5,888,241 A | 3/1999 | Jarvik | |
| 5,911,685 A | 6/1999 | Siess et al. | |
| 5,965,089 A * | 10/1999 | Jarvik | A61M 1/101 422/44 |
| 6,146,325 A | 11/2000 | Lewis et al. | |
| 6,176,822 B1 | 1/2001 | Nix et al. | |
| 6,200,260 B1 | 3/2001 | Bolling | |
| 6,227,820 B1 | 5/2001 | Jarvik | |
| 6,244,835 B1 | 6/2001 | Antaki et al. | |
| 6,254,359 B1 * | 7/2001 | Aber | F04D 3/02 417/356 |
| 6,344,022 B1 | 2/2002 | Jarvik | |
| 6,387,037 B1 | 5/2002 | Bolling et al. | |
| 6,390,969 B1 | 5/2002 | Bolling et al. | |
| 6,395,026 B1 | 5/2002 | Aboul-Hosn et al. | |
| 6,428,464 B1 | 8/2002 | Bolling | |
| 6,447,266 B2 | 9/2002 | Antaki et al. | |
| 6,530,876 B1 | 3/2003 | Spence | |
| 6,532,964 B2 | 3/2003 | Aboul-Hosn et al. | |
| 6,610,004 B2 | 8/2003 | Viole et al. | |
| 6,685,621 B2 | 2/2004 | Bolling et al. | |
| 6,716,189 B1 | 4/2004 | Jarvik et al. | |
| 6,719,791 B1 * | 4/2004 | Nusser | F16J 15/43 415/900 |
| 6,742,999 B1 * | 6/2004 | Nusser | F04D 3/02 417/423.1 |
| 6,761,532 B2 | 7/2004 | Capone et al. | |
| 6,889,082 B2 | 5/2005 | Bolling et al. | |
| 7,005,080 B2 | 2/2006 | Holland et al. | |
| 7,070,398 B2 | 7/2006 | Olsen et al. | |
| 7,144,364 B2 | 12/2006 | Barbut et al. | |
| 7,238,151 B2 * | 7/2007 | Frazier | A61M 1/1015 600/16 |
| 7,264,606 B2 | 9/2007 | Jarvik et al. | |
| 7,381,179 B2 | 6/2008 | Aboul-Hosn et al. | |
| 7,435,059 B2 | 10/2008 | Smith et al. | |
| 7,458,929 B2 | 12/2008 | Bolling et al. | |
| 7,468,050 B1 | 12/2008 | Kantrowitz | |
| 7,479,102 B2 | 1/2009 | Jarvik | |
| 7,544,160 B2 | 6/2009 | Gross | |
| 7,585,322 B2 | 9/2009 | Azzolina | |
| 7,614,997 B2 | 11/2009 | Bolling | |
| 7,699,586 B2 * | 4/2010 | LaRose | A61M 1/1017 417/356 |
| 8,777,832 B1 * | 7/2014 | Wang | A61M 1/1024 600/16 |
| 9,107,992 B2 * | 8/2015 | Kushwaha | A61F 2/82 |
| 9,314,557 B2 * | 4/2016 | Ricci | A61M 1/1015 |
| 9,623,162 B2 * | 4/2017 | Graham | A61M 1/122 |
| 9,717,833 B2 * | 8/2017 | McBride | A61M 1/122 |
| 9,726,195 B2 * | 8/2017 | Cecere | F04D 29/548 |
| 9,771,801 B2 * | 9/2017 | Schumacher | F01D 5/02 |
| 9,775,936 B2 * | 10/2017 | Wu | A61M 1/101 |
| 2001/0002234 A1 * | 5/2001 | Woodard | F01D 25/22 415/182.1 |
| 2001/0009645 A1 * | 7/2001 | Noda | F04D 3/02 417/355 |
| 2001/0031210 A1 * | 10/2001 | Antaki | F04D 3/005 417/356 |
| 2002/0147495 A1 * | 10/2002 | Petroff | A61M 1/106 623/3.25 |
| 2003/0021683 A1 * | 1/2003 | Capone | F04D 29/047 415/220 |
| 2003/0139643 A1 | 7/2003 | Smith et al. | |
| 2003/0228214 A1 * | 12/2003 | McBride | B63H 11/08 415/191 |
| 2004/0191116 A1 * | 9/2004 | Jarvik | A61M 1/101 422/44 |
| 2005/0135942 A1 * | 6/2005 | Wood | F16C 32/044 417/348 |
| 2006/0029495 A1 * | 2/2006 | Ishii | F04D 29/548 415/191 |
| 2007/0078293 A1 * | 4/2007 | Shambaugh, Jr. | A61M 1/101 600/16 |
| 2007/0100196 A1 * | 5/2007 | LaRose | A61M 1/101 600/16 |
| 2007/0156006 A1 * | 7/2007 | Smith | A61M 1/1031 600/16 |
| 2007/0253842 A1 | 11/2007 | Horvath et al. | |
| 2008/0269880 A1 * | 10/2008 | Jarvik | F04D 3/00 623/3.13 |
| 2008/0292478 A1 * | 11/2008 | Baykut | F04D 3/02 417/420 |
| 2009/0203957 A1 | 8/2009 | LaRose et al. | |
| 2009/0204205 A1 * | 8/2009 | LaRose | F04D 3/00 623/3.13 |
| 2009/0226328 A1 * | 9/2009 | Morello | A61M 1/1015 417/1 |
| 2009/0259308 A1 * | 10/2009 | Hidaka | F04D 13/06 623/3.13 |
| 2010/0121438 A1 * | 5/2010 | Jarvik | F04D 25/06 623/3.13 |
| 2010/0130809 A1 * | 5/2010 | Morello | A61M 1/1086 600/16 |
| 2010/0174131 A1 * | 7/2010 | Foster | A61M 1/1031 600/16 |
| 2011/0237863 A1 * | 9/2011 | Ricci | A61M 1/1015 600/16 |
| 2011/0238172 A1 * | 9/2011 | Akdis | A61M 1/101 623/3.11 |
| 2011/0311383 A1 * | 12/2011 | White | F04D 29/0413 417/423.7 |
| 2012/0003086 A1 | 1/2012 | Morris et al. | |
| 2012/0095281 A1 * | 4/2012 | Reichenbach | A61M 25/005 600/16 |
| 2012/0134793 A1 | 5/2012 | Wu et al. | |
| 2012/0134832 A1 * | 5/2012 | Wu | F04D 3/00 416/198 R |
| 2012/0245681 A1 * | 9/2012 | Casas | A61M 1/1086 623/3.28 |
| 2012/0291527 A1 * | 11/2012 | Graichen | G01N 11/16 73/54.25 |
| 2013/0209292 A1 * | 8/2013 | Baykut | F04D 3/00 417/420 |
| 2014/0079557 A1 * | 3/2014 | LaRose | A61M 1/1015 416/223 R |
| 2014/0341726 A1 * | 11/2014 | Wu | A61M 1/101 415/199.5 |
| 2016/0228629 A1 * | 8/2016 | Graham | A61M 1/122 |
| 2016/0279311 A1 * | 9/2016 | Cecere | F04D 3/02 |
| 2018/0100507 A1 * | 4/2018 | Wu | F04D 3/00 |

FOREIGN PATENT DOCUMENTS

| | | | | |
|---|---|---|---|---|
| EP | | 0847767 A1 * | 6/1998 | ............. A61M 1/10 |
| JP | | 2004346930 A * | 12/2004 | .......... A61M 1/1015 |

(56) References Cited

FOREIGN PATENT DOCUMENTS

| | | | | |
|---|---|---|---|---|
| JP | 2004351213 A * | 12/2004 | .......... | A61M 1/1015 |
| WO | 9409274 A1 | 4/1994 | | |
| WO | WO 9934847 A2 * | 7/1999 | .......... | A61M 1/1005 |
| WO | 2005030296 A2 | 4/2005 | | |
| WO | WO 2005030296 A2 * | 4/2005 | ............... | F04D 3/00 |
| WO | WO 2007105842 A1 * | 9/2007 | .......... | A61M 1/1031 |
| WO | 2010036815 A2 | 4/2010 | | |
| WO | 2012054435 A1 | 4/2012 | | |
| WO | 2012054490 A1 | 4/2012 | | |
| WO | WO 2012112129 A1 * | 8/2012 | .......... | A61M 1/1015 |

OTHER PUBLICATIONS

PCT International Search Report for International Patent Application No. PCT/US2011/056722 dated Jan. 23, 2012 (5 pages).

Jeongho Kim, PhD, Multiphase CFD Analysis and Shape-Optimization of Blood-Contacting Medical Devices. Doctoral dissertation in the Department Biomedical Engineering at Carnegie Mellon University, Pittsburgh, PA, dated Aug. 2012.This thesis dissertation was presented publicly on the date cited above, previously advertised as a public presentation. Proof of publication can be found on the Biomedical Engineering Department website https://www.bme.cmu.edu/gradprog/PhDthesis.html. This publication may be obtained through the publicly available Carnegie Mellon Library website at the following link—http://search.library.cmu.edu/vufind/Resource/Results?lookfor=Jeongho+Kim.†

James Antaki et al. << Computational Design of The Fourth Pediaflowtm Pediatric Ventricular Assist Device>> Annual Meeting of the American Society of Artificial Organs, Washington, DC, Jun. 11, 2011 Proof of this public presentation is available in the archived edition of the conference program, available at http://asaio.com/wp-content/uploads/2012/08/2011-ASAIO-Annual-Conference-Program.pdf.†

* cited by examiner
† cited by third party

BLOOD PUMP WITH SEPARATE MIXED-FLOW AND AXIAL-FLOW IMPELLER STAGES AND MULTI-STAGE STATORS

CROSS-REFERENCE TO RELATED APPLICATIONS

This application claims the benefit of the filing date of U.S. Provisional Patent Application No. 61/823,224 filed May 14, 2013, the disclosure of which is incorporated by reference herein.

BACKGROUND OF THE INVENTION

Technical Field

This invention relates generally to pumps. More specifically, this invention relates to blood pumps, such as cardiac assist pumps that may be implanted in a patient.

Description of the Related Art

Rotordynamic pumps, such as centrifugal, mixed-flow, and axial-flow pumps with mechanical bearings or magnetically suspended systems, have been widely used as a ventricular assist devices to support patients with heart diseases. In magnetically levitated blood pumps, which generally include an impeller that is both magnetically suspended and rotated without mechanical means, an annular gap located between the rotor and stator suspension and drive components is conventionally designed to be relatively small. A narrow annular flow gap generally necessitates higher rotational speeds of the rotor in order to generate the desired pressure rise and flow rates needed to support patients. One challenge of operating a rotor at high rotational speeds is a tendency for high turbulence flow characteristics within the blood (e.g., high shear stress) that can increase the extent and rate of red blood cell damage.

Additionally, for centrifugal or mixed-flow blood pumps with shrouded impellers (i.e., a circumferentially revolved surface interconnecting the impeller blade tips), the fluid within the clearance space between a rotating front shroud and the stationary housing demonstrates a complex three-dimensional structure, leading to retrograde leakage flow and strong disk friction loss. The combination of disk friction loss and the strong vortical flow can lower pump efficiency and in some cases carry greater risks of hemolysis and thrombosis. A similar flow pattern can also occur at the back clearance space between a rotating back shroud and the stationary housing for centrifugal or mixed flow pumps with or without a front shroud. The level of shear stress within the clearance between the walls of a shroud and housing depends, at least in part, on the pump rotational speed.

For centrifugal or mixed-flow blood pumps with unshrouded or semi-open impellers, the lack of a front shroud introduces a problem due to the blade tip leakage flow from pressure-side to suction-side of the blades which occurs through the clearance between the rotating blade tip and the stationary housing. The leakage flow can also generate a jet leakage vortex that interacts with the primary flow, causing hydraulic loss and possibly inducing blood trauma. The shear stress exhibited in the gap or clearance between the blade tip gap and the stationary housing is very sensitive to the pump rotational speed as well as the magnitude of the gap itself.

For axial flow blood pumps with completely magnetically suspended systems, the annular gap located between the cylindrical rotor and housing has to be small enough to maintain the magnetic radial stiffness. Additionally, the axial length of the rotor has to be sized to maintain proper stability, exhibiting sufficient axial stiffness and little yaw. Such an arrangement generally leads to the requirement for high pump speed in order to generate the required pressure rise and flow rate for patients. However, the shear stress exhibited by the fluid within the annular gap region can become very high due to the high rotational speed and the narrowness of the gap. Moreover, conventional designs of axial blood pumps tend to have very long blade profiles (i.e., extending long axial distances and having very large blade wrap angle) and large trailing edge angles (i.e., β2 close to 90 degrees). Such a design with very long blade profiles not only increases the blade tip areas with higher shear stress but also leads to flow separation and vortices, particularly at the off-design conditions.

In view of the foregoing, further improvements in rotor-dynamic pumps can be provided.

SUMMARY OF THE INVENTION

Various embodiments of rotordynamic pumps for fluids are set forth herein in accordance with the present invention.

Exemplary embodiments may provide an apparatus and method for a multistage fluid pump for pumping a fluid such as blood or other fluid, in which a pump has a rotor hub having leading and trailing portions adjacent an inlet and an outlet of the pump, respectively, and an intermediate portion between the leading and trailing portions. A rotor stage comprising at least one impeller blade is positioned at the leading portion of the pump. A stator stage comprising at least one stator blade extends radially inward from a stator housing in a portion of a fluid pathway that surrounds the intermediate portion and is configured to reduce a circumferential component of a flow. As used herein, "radial" or "radially" mean in a radial direction away from a rotational axis of the pump. An axial dimension of the at least one stator blade is smaller than a diameter of the intermediate portion of the rotor hub. As used herein, "axial" dimension means a dimension along or parallel to the pump's rotational axis. A reduced axial dimension of the stator blade reduces contact between the stator blade and components of a fluid, such as red blood cells, for example, and may help reduce risk of damage to red blood cells over time. A second stator stage comprising at least one second stage stator blade may be positioned in a trailing pathway portion of the fluid pathway that surrounds the trailing portion of the rotor, and may reduce a circumferential component of a flow. In a particular example, a transitional outflow region of the stator housing encompassing the trailing pathway portion may define an interior conical space and the at least one second stage stator blade can extend inwardly into the conical space.

High efficiency, low blood damage, and small compact size are often desirable features for a long-term implantable blood pump. A reduction in the size of the pump may be facilitated by a stator blade positioned within an intermediate fluid pathway portion for reducing a circumferential component of the flow, thereby improving a rotational stability of the pump, and possibly allowing the pump to operate with smaller, more lightweight, or less complicated bearings. A reduction in risk of blood cell damage may be facilitated by a stator blade configuration in which each stator blade has a smaller axial dimension than heretofore contemplated, such as an axial dimension that is less than a diameter of an intermediate portion of the rotor hub. Red blood cell damage in blood pumps is mainly related to the shear stress and degree to which the red blood cells contact other surfaces such as impeller blades and stator blades when passing through the flow paths.

Efficiency may also be improved when fluid is directed through a first stage rotating mixed-flow type impeller to gain both kinetic energy and pressure rise and then further to gain kinetic energy and pressure rise from passage through second rotating axial impeller region after passage through the stator blade region. Such operation may yield a total higher head (i.e., pressure rise) at the same pump speed than a single stage mixed-flow or single axial flow configuration thus resulting in increased pump efficiency. Alternatively, it may be possible to operate the multiple impeller stage pump at a lower speed and produce the same pressure rise as a single impeller stage configuration. The higher efficiency provides the benefit of low temperature rise of the motor and longer battery life. As contact with bodily tissues is inherent to the device, the reduction in operating temperatures can reduce risks associated with contact to surrounding body tissues. In addition, higher shear stress regions in blood pumps usually occur in the blade tip gap regions, which are directly related to the pump speed. A two-stage impeller design requires a lower pump speed than a purely single stage mixed-flow or axial flow blood pump in order to generate about 150 mmHg pressure rise for the need of a human body.

BRIEF DESCRIPTION OF THE DRAWINGS

The foregoing and other advantages of the invention will become apparent upon reading the following detailed description and upon reference to the drawings in which.

DETAILED DESCRIPTION OF THE INVENTION

For purpose of illustration, discussions of the technology will be made in reference to its utility as a cardiac assist blood pump. However, it is to be understood that the technology may have a variety of wide applications to many types of turbomachinery including, for example, commercial and industrial pumps, compressors, and turbines.

Figure 1:
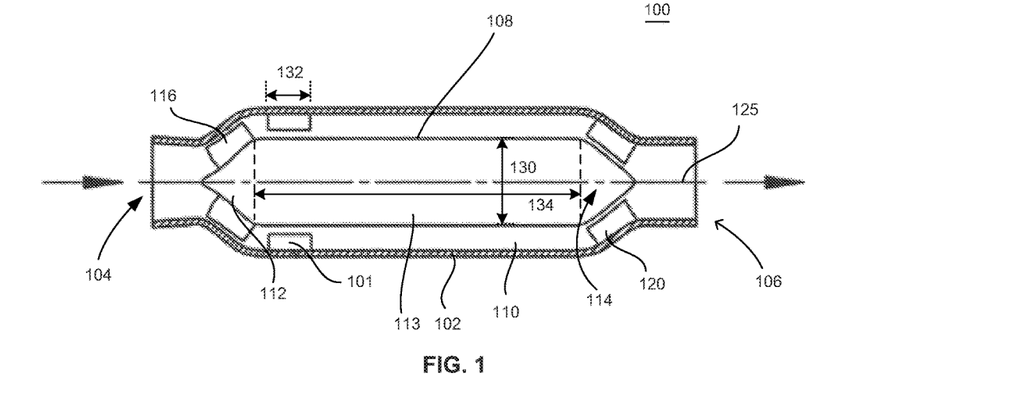
FIG. 1 is a longitudinal cross-sectional (meridional) view of a pump in accordance with an embodiment of the invention.
Figure 2:
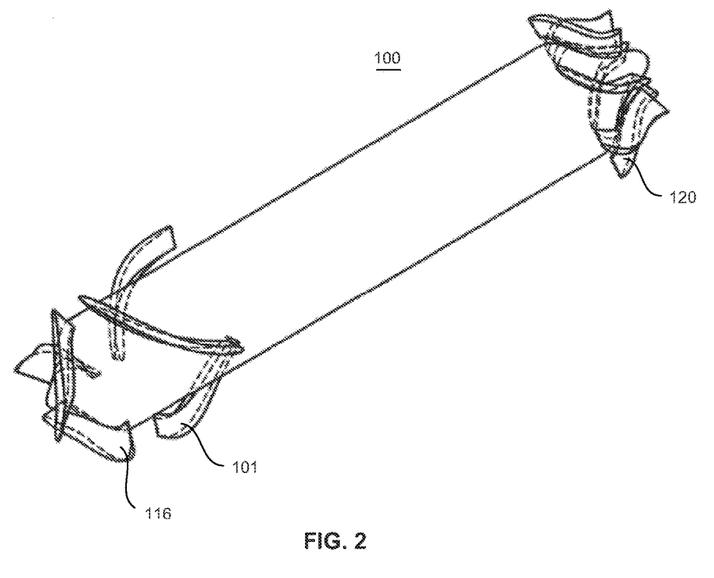
FIG. 2 is a perspective view of various components of the pump shown in FIG. 1.
Figure 3:
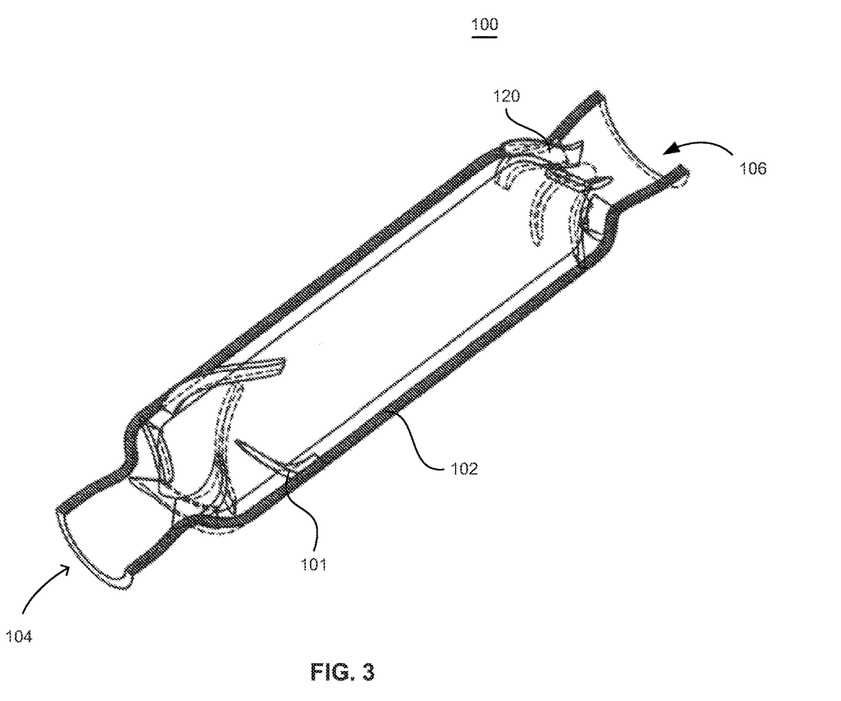
FIG. 3 is a perspective view of various components of the pump shown in FIG. 1 including with a partial cross-sectional view of a housing member.

Referring to FIGS. 1 through 3, a rotordynamic blood pump 100 is shown in accordance with an embodiment of the present invention. FIG. 1 shows a meridional section of the pump 100. FIG. 2 shows a perspective view of various components of the pump, the housing of the pump being removed from the view for purposes of clarity. FIG. 3 shows a perspective view of the pump 100 with the housing being sectioned to provide context to other components of the pump 100. Aspects of rotordynamic blood pumps are disclosed in co-pending U.S. patent application Ser. No. 13/275,912 filed Oct. 18, 2011, and 13/276,009 filed Oct. 18, 2011, the disclosures of which are incorporated herein by reference.

The pump 100 includes a stator housing 102 having an inlet 104 and an outlet 106. A rotor hub 108 having a generally cylindrical configuration is disposed within an interior volume defined by the housing such that a fluid pathway includes an intermediate pathway portion 110 which defines an annulus or annular gap ("annulus" and "gap" also referenced herein by "110") surrounding the rotor hub 108 within the stator housing 102. The rotor hub 108 includes a leading portion 112 (i.e., leading with respect to intended fluid flow through the pump 100), that may exhibit a generally conical geometry and that is positioned near the inlet 104. Additionally, the rotor hub 108 includes a trailing portion 114 (i.e., trailing with respect to intended fluid flow through the pump 100) that exhibits a generally conical geometry and that is positioned near the outlet 106. An intermediate portion 113 of the rotor hub extends between the leading and trailing portions 112, 114 of the rotor hub. The intermediate portion 113 may be substantially cylindrical in shape, having a diameter extending through an axis of the rotor hub. The leading portion 112 may have a diameter which increases with a distance from the inlet to a diameter of the intermediate portion 113. The trailing portion 114 may have a diameter which decreases with proximity to the outlet 106; i.e., the diameter of the trailing portion may decrease with a distance from the intermediate portion 113.

The pump 100 is configured with one or more impeller blades 116 associated with the first, mixed-flow stage which can be formed on, or otherwise coupled with, the rotor hub 108 along the leading portion 112 (i.e., in the conical region). Impeller blades 116 are positioned within a leading pathway portion of the fluid pathway in a space between the leading portion of the rotor hub 108 and the stator housing 102, providing suction to the fluid entering the inlet 104 and delivering the fluid in both an axial and a radially outward direction into an intermediate pathway portion 110 of the pump. The flow driven by the impeller blades 116 into the intermediate pathway portion has an axial component in a direction parallel to a rotational axis 125 of the rotor hub, and also has a substantial circumferential component in a direction of a circumference of the intermediate portion 113 of the rotor hub.

In the embodiment shown in FIG. 1, impeller blades 116 can be unshrouded. An unshrouded configuration may provide savings in cost and also reduce the complexity of manufacturing such a pump. However, in other embodiments shrouds may be incorporated into the impeller designs. In an unshrouded configuration, a gap or clearance is maintained between lengthwise upper surface of the rotating impeller blades and the stationary stator housing.

As seen in FIG. 1, the intermediate portion 113 of the rotor hub has an axial dimension 134 which is greater than a diameter 130 of the intermediate portion. Axial dimension is also referred to herein as "meridional length." The axial dimension 134 corresponds to a total annular gap length, i.e., length of the gap 110 between the intermediate portion 113 of the rotor and an inner wall of the stator housing 102 in an axial direction of the rotor hub. In accordance with one embodiment of the invention, pump 100 can be configured with magnetic bearings which eliminate the need for a mechanically bound and lubricated central shaft on which the rotor hub rotates during operation. Rather, magnetic bearings have a set of opposing rotor and stator magnets at positions near the ends of the rotor hub (i.e., ends corresponding to the leading and trailing portions 112, 114) which magnetically suspend the rotor hub 108 within the fluid pathway within the stator housing 102. During operation of the pump, the magnets repel each other to maintain the rotational axis 125 of the rotor hub 108 in a stable radial position within the stator housing 102.

The circumferential component of the flow within the intermediate pathway portion 110 of the pump produces whirl forces which can negatively impact the rotational stability of the pump 100, particularly a pump having magnetic bearings. The inventors have found that high whirl forces can have a destabilizing effect on rotation of a rotor, which if unchecked could cause the rotational axis of a magnetically suspended rotor to whip and result in touchdown of the rotor. High whirl forces can be overcome by providing larger magnetic bearings, but larger magnetic bearings typically increase the size and weight of the pump which is less desirable from a surgical perspective.

It is noted that both the radial clearance and the axial dimension 134 of the intermediate pathway portion 110, also referred to herein as annulus or annular gap can have a significant effect on pump performance and possible blood damage. For a magnetically suspended and rotated blood pump, the sizing of the annulus also has an effect on the radial and yaw stiffness of the suspension system. From a view point of hydrodynamics, the radial gap (i.e., dimension of the annulus in the radial direction) the annulus should be made as large as reasonably possible, while for the consideration of magnetic suspension system, the radial gap of the annulus should be small enough, and the axial length of the annulus should be long enough, to maintain a stable rotation of the rotor hub 106 within the stator housing 102. Improper design of such components, including the size of the annulus and the flow characteristics of the fluid passing through the annulus can lead to the rotor hub 106 being unstable and exhibiting, for example, a whip phenomenon as it rotates within the stator housing 102 when configured as a magnetically suspended or "levitated" pump.

It is noted that the components of the pump 100 are shown in relatively simplistic forms for sake of clarity in the associated description. For example, the magnetic and electronic components that might be utilized in association with a magnetically levitated pump are not specifically shown. However, one of ordinary skill in the art will recognize that such components will be inherently placed in or adjacent to the stator housing 102 and within the rotor hub 108 to provide such a magnetically levitated and rotated pump. One example of a completely magnetically suspended system associated with a pump is described in U.S. Patent Application Publication No. 20110237863 entitled "Magnetically Levitated Blood Pump With Optimization Method Enabling Miniaturization", the disclosure of which is incorporated by reference herein.

The inventors have discovered that whirl forces within the pump can be decreased, and the rotational stability of the pump can be increased by configuring the stator with one or more stator blades 101 for reducing a circumferential component of a flow into the intermediate pathway portion 110 of the pump from the one or more impeller blades 116 of the leading portion upstream therefrom. The stator blades 101, disposed on an inner surface of the stator housing 102 or mechanically coupled to the stator, and projecting within the intermediate pathway portion 110, typically twist in a direction opposite that in which the impeller blades twist. In this way, the stator blades 101 help to recover kinetic energy of the fluid (e.g., blood) and lead the fluid to flow in a more axial direction through the pump towards the outlet 106.

A gap or clearance exists between the lengthwise lower surface of the stator blades 101 and the rotor hub 108. The extent of both the impeller blade 116 tip clearances and the stator blade 101 tip clearances can have significant effects on the pump's performance including, for example, pump head and efficiency. Additionally, these clearances can have a significant impact on the amount of damage that may occur to the blood cells. In one particular embodiment, both the impeller blade tip clearances and the stator blade tip clearances may be approximately 0.1 mm to approximately 0.2 mm. However, the clearances may be set at other distances depending on a variety of factors.

In one embodiment, the stator stage can be disposed within the intermediate pathway portion 110 of the pump at a position as close as possible to the leading portion 112. In this way, whirl forces generated by a circumferential component of the flow coming off of the rotor stage can be reduced closer to an entrance within the intermediate pathway portion 110. In one embodiment, an axial dimension 132 of the at least one stator blade 101 can be any length from about 2% to 98% of the total annular gap length in the axial direction. Stator blades which are longer and extend to greater meridional lengths can have greater efficiency in reducing whirl forces surrounding the intermediate portion of the rotor hub, and in recovering pressure to increase the pump head and efficiency. In a pump 100 as seen in FIGS. 1-3, an axial dimension of the intermediate portion is greater than a diameter 130 of the intermediate portion of the rotor hub 108. The inventors have found that reducing the axial dimension 132 of the one or more stator blades 101 to a value that is less than the diameter 130 of the intermediate portion, this can help reduce damage to blood during operation of the pump.

Downstream of the first stage stator blades 101, adjacent the pump outlet 106 and the trailing portion 114 of the rotor hub 108, one or more second stage stator blades 120 can extend from an inner surface of the stator housing 102. The stator blades 120 help to recover kinetic energy of the fluid (e.g., blood) and lead the fluid to flow axially through the outlet 106. A gap or clearance exists between the lengthwise lower surface of the stator blades 120 and the trailing portion 114 of the rotor hub 108. The stator blades 120 also help to reduce turbulence that might develop during transition of the flow from the annulus 110 through the outlet 106. As with the stator blade 101 tip clearances described above, the extent of the stator blade 120 tip clearances can have significant effects on the pump's performance including, for example, pump head and efficiency. Additionally, these clearances can have a significant impact on the amount of damage that may occur to the blood cells. In one particular embodiment, the clearances of each of the impeller blade tips and the tips of the stator blades 101 and 120 may be approximately 0.1 mm to approximately 0.2 mm. However, the clearances may be set at other distances depending on a variety of factors.

During operation of the pump, fluid enters through the inlet 104 of the pump 100 and encounters the first-stage impeller blades 116. The pressure of the fluid is raised by the first-stage impeller blades 116 and directed both radially outward and axially forward into the intermediate pathway portion 110 between the stator housing 102 and the rotor hub 108. The fluid then encounters the stator blades 101 which help to capture some of the kinetic energy of the fluid and direct the fluid in more of an axial direction of the pump 100.

After the fluid (e.g., blood) passes the stator blades 101 within the intermediate pathway portion as it travels towards the outlet, the fluid tends to regain momentum in a circumferential direction, due to rotation of the rotor hub 108 and a viscosity characteristic of the fluid. The second stage stator blades 120 again help convert some of the kinetic energy of the fluid into pressure at the outlet 106, by reducing the circumferential component of the momentum such that the fluid is directed more in an axial direction of the pump. In this way, the fluid flowing through the outlet 106 is directed in more of an axial direction of the pump.

Still referring to FIGS. 1-3, it is seen that the pump may include three (3) first-stage impeller blades 116 of mixed-flow type, three (3) first-stage stator blades 101 of axial-flow type, and four stator blades 120. Of course, it is contemplated that other arrangements having more or fewer impeller blades 116 or stator blades 101, 120 may be utilized. The impeller blades 116 and the first and second stage stator blades 101, 120 all have 3-dimensional curved surfaces which can be designed, for example, using conventional turbomachinery inverse design theory such as 2D or quasi-3D methods. Their shapes and numbers may also be optimized via computational fluid dynamics (CFD) to reach the highest efficiency with minimal blood damage.

Another feature of the embodiment of FIGS. 1-3 is that pump operation can be provided by the single-stage impeller blades 116, since no other stage of impeller blades need be provided. Specifically, in the embodiment of FIGS. 1-3, there is no impeller blade in the intermediate pathway portion 110 between the first-stage stator blades 132 and the second-stage stator blades 120. In this way, the second-stage stator blades may help to reduce a circumferential component of a flow received from the first stator stage, wherein the flow is in a form undriven by an impeller blade between the first and second stator stages. In addition, with the pump shown in FIGS. 1-3, the flow from inlet 104 to the outlet 106 may be driven substantially only by a single rotor stage having the at least one impeller blade 116. Downstream stator blades 101 reduce a circumferential component of the flow as the fluid travels towards the outlet. Second stage stator blades 120, if present, may also help reduce a circumferential component of the flow as the fluid is delivered to the outlet 106.

In one particular embodiment, the pump 100 may be configured as an implantable blood pump wherein the rotor hub 108 is magnetically suspended and rotated. The rotor hub 108 may exhibit and overall length of approximately 106 mm and a diameter 130 of approximately 12.4 mm. The inside diameter of the stator housing 102 may be approximately 16 mm, resulting in a clearance gap (for the intermediate pathway portion 110 or annulus) of approximately 1.8 mm between rotor hub 108 and the inner surface of the stator housing 102. The inlet 104 and outlet 106 may each exhibit a diameter of approximately 8 mm. In such an embodiment, it has been calculated that blood entering the inlet 104 at a total pressure (i.e., kinetic pressure plus static pressure) of approximately 0 millimeters of mercury (mmHg), and at a flow rate of approximately 5 liters per minute (LPM), will experience a total increase of pressure of approximately 190 mmHg when it flows through the impeller blades 116 with the rotor hub 108 rotating at a speed of approximately 16,000 rotations per minute (RPM). Though the fluid experiences head loss as it flows through the remainder of the pump, the stator blades 101, 120 will help to capture kinetic energy and convert it into pressure while also directing the flow of the fluid in a more axial direction and reducing a circumferential component of the flow. Thus, while the fluid pressure may decrease as the fluid moves downstream from the impeller, the stator blades can serve to reduce turbulence such that the pressure of the fluid leaving the outlet 106 will be approximately 190 mmHg. Of course, such an example is not to be considered limiting in any sense. The pump 100 may be configured to exhibit different dimensions, operate at different rotational speeds, and process fluid at different flow rates and pressures.

Figure 4:
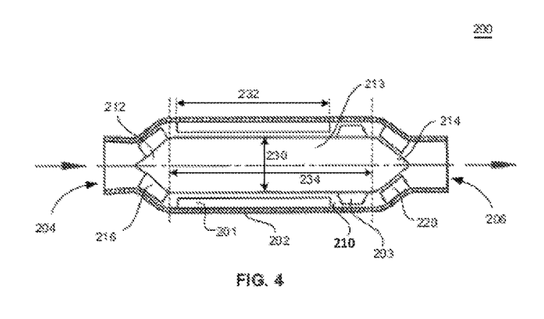
FIG. 4 is a longitudinal cross-sectional (meridional) view showing a configuration of a pump in accordance with another embodiment of the invention.
Figure 5:
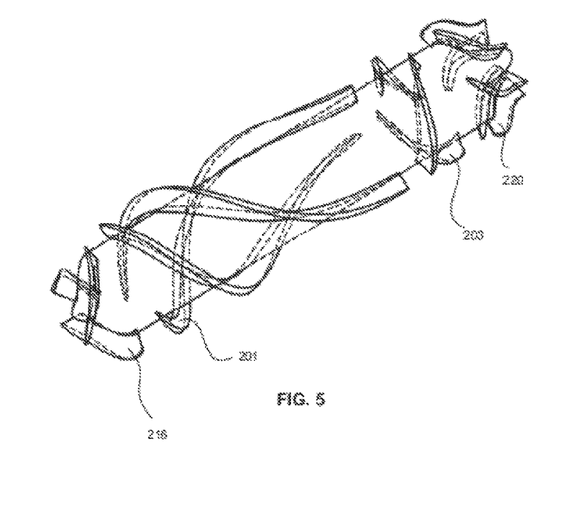
FIG. 5 is a perspective view of various components of the pump shown in FIG. 4.
Figure 6:
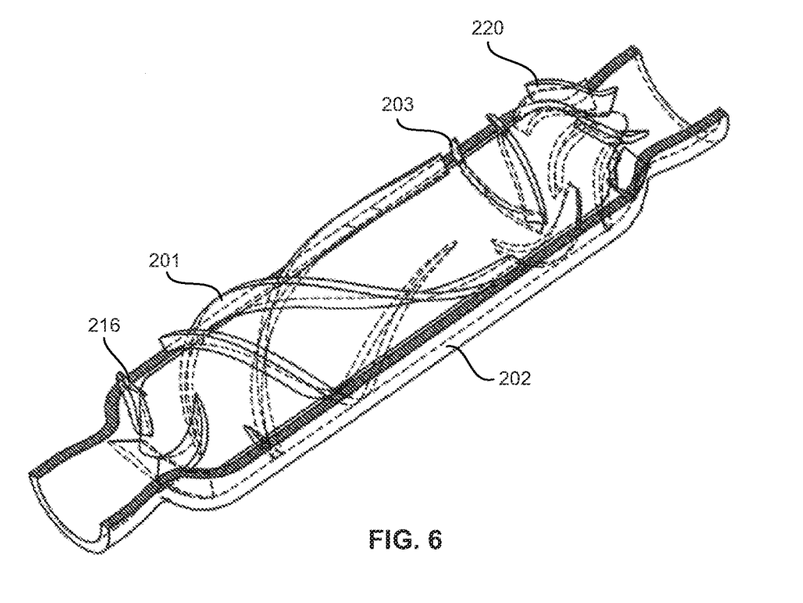
FIG. 6 is a perspective view of various components of the pump shown in FIG. 4 including with a partial cross-sectional view of a housing member.

Referring to FIGS. 4-6, another example of a pump 200 is seen. In this case, a two-stage impeller configuration is employed which may include three (3) first-stage impeller blades 216 of mixed-flow type, three first-stage stator blades 201, three (3) second-stage impeller blades 203 of axial-flow type, and four stator blades 220. Of course, it is contemplated that other arrangements having more or fewer impeller blades 216, 203 at each stage or fewer stator blades 201, 220 may be utilized. The shapes and numbers of the impeller blades and stator blades may also be optimized via computational fluid dynamics (CFD) to reach the highest efficiency with minimal blood damage. In one example, the mixed-flow first-stage impeller blades 216 and the axial-flow second-stage impeller blades 203 may be designed, with respect to the head, such that the first stage provides approximately 50% to approximately 70% of the total pump head, while the second stage may provide approximately 30% to approximately 50% of the total pump head.

The leading edge angle of stage-two impeller blades 203 along each streamline may be set to be approximately equal to the trailing edge angle of the first-stage impeller blades 216 with a plus or minus attack angle of 0° to 5° by inverse design theory and CFD optimization in accordance with the flow modified by stator blades 201 so that the flow from the stator blades 201 matches well with the leading edge of the second stage impeller blades 203. The second stage blades 203 may be designed by aerofoil cascade theory together with CFD optimization to avoid complex and unreasonable very long blades. The stator blades 220 may be designed so that the leading edge angles generally match the flow out of the stage-two impeller blades 203. The trailing edge angles of the stator blades 220 may be approximately 90° so that the blood or other fluid can be led to the outlet substantially uniformly without minimal turbulence. The blade-to-blade sections and the meridional section part near the stator blades 220 (as depicted in FIG. 4) may be designed and optimized by CFD so that they can further recover some potential energy (pressure) from the kinetic energy of the fluid flow.

It is noted that the second-stage impeller blades are positioned downstream within the annulus 210 nearer to the second stage stator blades 220 than to the first-stage impeller blades 216. Stated another way, the second-stage impeller blades 203 are positioned nearer to trailing portion 214 of the rotor hub 208 than to the leading portion 212 of the rotor hub 208 (and nearer to the inlet 204 than to the outlet 206). The positioning of the second-stage impeller blades 203 nearer to the trailing portion 214 may provide greater stabilization to the rotor hub 208 during operation of the pump 200 so as to minimize or prevent any whip phenomenon that might occur. For example, because of the increase in circumferential velocity of the fluid imposed by the second-stage impellers, when the second-stage impeller blades 203 are positioned nearer to the leading portion, the rotor hub under certain operating conditions may experience a whip phenomenon and exhibits signs of instability. In the embodiment shown in FIG. 6, the second-stage impeller blades 203 can boost the pressure and flow rate (as with the configuration described with respect to FIGS. 1-3) while providing increased stability because the increased circumferential velocity imparted by the second-stage impeller blades 203 will be converted, nearly immediately, into pressure by the stator blades 220 and the circumferential velocity will be significantly reduced, to nearly zero, as the fluid flows out from the stator blades 220.

Referring again to FIG. 4, in another embodiment which is not specifically shown therein, but which is a variation of the above-described embodiment, the second-stage impeller blades 203 are omitted. Stator blades 201 are relatively long, having axial dimensions 232 which are substantial in relation to an axial dimension 234 of the intermediate pathway portion 210 of the pump. Such stator blades 201, whose axial dimensions can be greater than the diameter 230 of the intermediate portion 213 of the rotor, and in some cases, greater than half the axial dimension 234 of the intermediate portion 213, are longer than the stator blades 101 in the embodiment described above with respect to FIGS. 1-3.

In this variation, a flow from the inlet 204 to the outlet 206 of the pump is driven substantially only by impeller blades 216 of the rotor stage at the leading portion 212. Stator blades 201 which are relatively long, i.e., longer than those of the FIGS. 1-3 embodiment, help to straighten the flow through a longer portion of the intermediate pathway portion 210 by reducing a circumferential component of the flow, and may further help to reduce whirl forces within the pump 200. Optional stator blades 220, if present at the trailing portion, may further help to straighten the flow, reducing a circumferential component thereof, as the fluid leaves the intermediate pathway portion 210 and is delivered to outlet 206.

Figure 7:
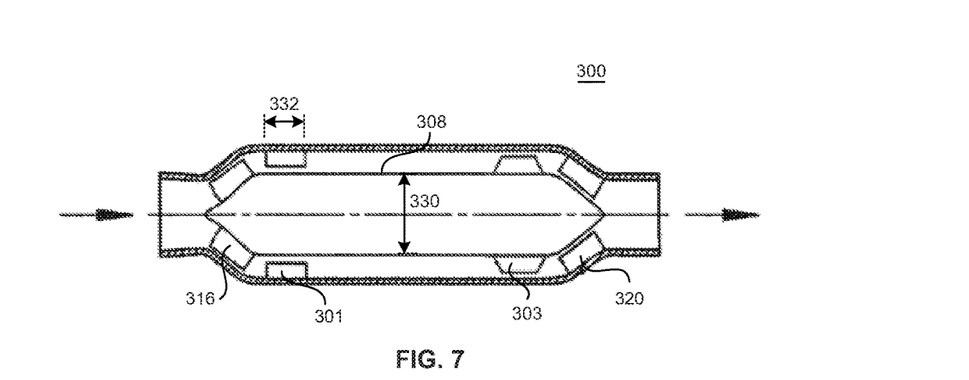
FIG. 7 is a longitudinal cross-sectional (meridional) view further showing a pump in accordance with a variation of the embodiment of the invention illustrated in FIGS. 1, 2 and 3.

Referring now to FIG. 7, a two impeller stage pump 300 is shown in accordance with a variation of the embodiment described above with reference to FIGS. 4, 5 and 6, having a first stage of impeller blades 316 and a second stage of impeller blades 303, and having a first stage of stator blades 301 and a second stage of stator blades 320. In this variation, an axial dimension 332 of the first-stage stator blades 301 is smaller than a diameter 330 of the intermediate portion of the rotor hub 308. This aspect of pump 300 is more similar to the configuration seen in the embodiment described above with respect to FIGS. 1, 2 and 3 which have a like configuration of stator blades 301. In this case, the two impeller-stage configuration can have increased pumping efficiency, which may facilitate lower speed operation relative to the configuration seen, for example, in the pump 100 of FIGS. 1-3. In addition, stator blades 301 having an axial dimension 332 shorter than the diameter 330 of the intermediate portion may help to reduce contact of the blades 301 with the blood and may help reduce damage to the blood.

Figure 8:
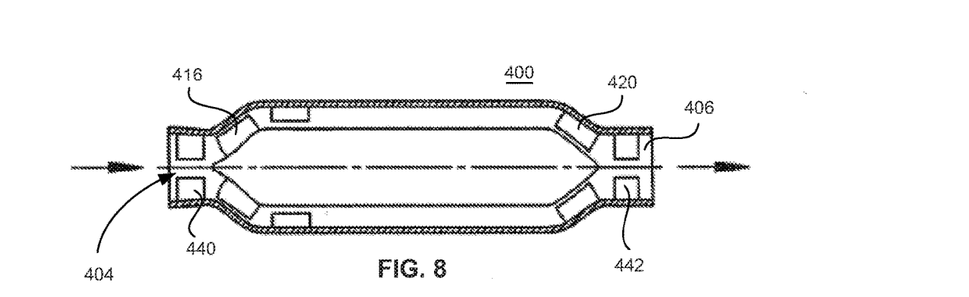
FIG. 8 is a longitudinal cross-sectional (meridional) view of a pump in accordance with further embodiment of the invention.

FIG. 8 illustrates a further variation of the embodiment shown and described above relative to FIGS. 1-3 in which additional stator blades 440 or vanes can be provided within the inlet 404 of the pump, these helping to reduce pre-rotation for the blood before entering the leading pathway portion surrounding the impeller blades 416. Such inlet blades 440 can be of particular benefit in off-design conditions such as with very small rate of flow through the pump. Additional blades 442 within the outlet 406 of the pump can also further help to straighten the flow from the blades 420 of the second stator stage to recover static pressure at the outlet 406 of the pump 400.

Figure 9:
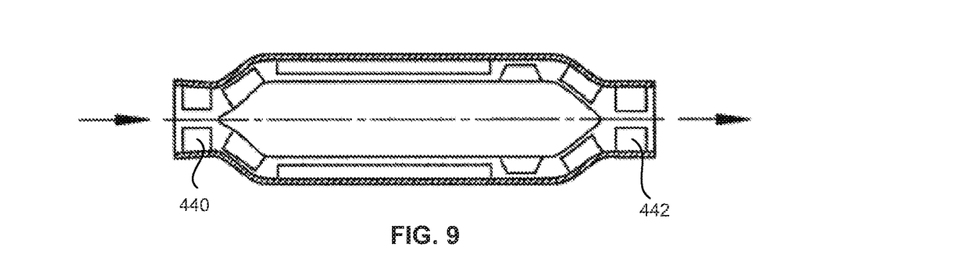
FIG. 9 is a longitudinal cross-sectional (meridional) view showing a configuration of a pump in accordance with yet another embodiment of the invention.

FIG. 9 illustrates a further variation in which an additional inlet stage of stator blades 440 and an outlet stage of stator blades 442, such as seen in FIG. 8, are provided in a pump having a configuration such as described above with respect to FIGS. 4-6.

Figure 10:
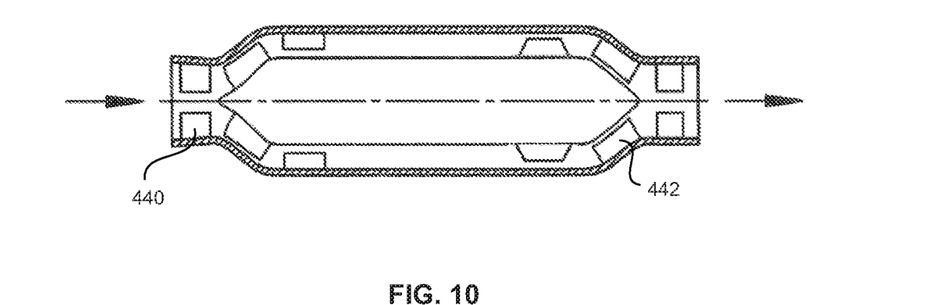
FIG. 10 is a longitudinal cross-sectional (meridional) view further showing a pump in accordance with the embodiment illustrated in FIG. 9.

FIG. 10 illustrates a further variation in which an additional inlet stage of stator blades 440 and an outlet stage of stator blades 442, such as seen in FIG. 8, are provided in a pump having a configuration such as described above with respect to FIG. 7.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims. It is specifically noted that any features or aspects of a given embodiment described above may be combined with any other features or aspects of other described embodiments, without limitation.

The invention claimed is:

1. A blood pump configured to provide continuous fluid flow, comprising:
   a stator housing having an inlet and an outlet;
   a rotor hub defining a rotational axis extending from the inlet to the outlet and comprising a body having a leading portion positioned adjacent the inlet, a trailing portion positioned adjacent the outlet, an intermediate portion extending between the leading portion and the trailing portion, and a fluid pathway of the pump extends from the inlet to the outlet along the rotor hub;
   an inlet stator blade extending radially inward from the stator housing within the inlet, the inlet stator blade including a distal-most portion extending along the rotational axis to define the fluid pathway;
   a rotor stage positioned at the leading portion, the rotor stage having at least one impeller blade configured to drive a circumferential component and an axial component of a flow into an intermediate pathway portion of the fluid pathway surrounding the intermediate portion; and
   a stator stage comprising at least one stator blade extending radially inward from the stator housing in the intermediate pathway portion and defining a gap between the at least one stator blade and the rotor hub, the stator stage configured to reduce the circumferential component of the flow;
   an axial dimension of the intermediate portion being greater than a diameter of the intermediate portion; and
   an axial length of each of the at least one stator blade being smaller than the diameter of the intermediate portion.

2. The blood pump as claimed in claim 1 wherein the stator stage is a first stator stage, further comprising a second stator stage having at least one stator blade extending radially inward from the stator housing in a trailing pathway portion of the fluid pathway surrounding the trailing portion, the second stator stage configured to reduce a circumferential component of the flow.

3. The blood pump as claimed in claim 2, wherein the second stator stage is configured to reduce a circumferential component of the flow within the fluid pathway received from the first stator stage.

4. The blood pump as claimed in claim 2, wherein a portion of the stator housing adjacent the trailing portion decreases in diameter with proximity to the outlet.

5. The pump as claimed in claim 2, wherein the inlet stator blade is configured to reduce a circumferential component of the flow.

6. The blood pump as claimed in claim 2, further comprising at least one outlet stator blade extending radially inward from the stator housing within the outlet and configured to reduce a circumferential component of the flow.

7. The blood pump as claimed in claim 2, further comprising a second rotor stage comprising at least one second stage impeller blade positioned on the intermediate portion between the first and second stator stages.

8. The blood pump as claimed in claim 7, wherein the second stator stage is configured to reduce a circumferential component of the flow modified by the second rotor stage.

9. The blood pump of claim 7, wherein the at least one second stage impeller blade is positioned closer to the inlet than to the outlet.

10. The blood pump of claim 1, wherein the at least one second-stage impeller blade is positioned closer to the outlet than to the inlet.

11. The blood pump of claim 1, wherein the rotor hub and the stator housing are configured of blood compatible materials.

12. The blood pump of claim 1, wherein the rotor hub is configured to be magnetically suspended and rotated by the stator during operation of the pump.

13. A blood pump configured to provide continuous fluid flow, the blood pump comprising:
a stator housing having an inlet and an outlet;
a rotor hub defining a rotational axis extending from the inlet to the outlet and comprising a body having a leading portion positioned adjacent the inlet, a trailing portion positioned adjacent the outlet, and an intermediate portion extending between the leading portion and the trailing portion, and a fluid pathway of the pump extends from the inlet to the outlet along the rotor hub;
an inlet stator blade extending radially inward from the stator housing within the inlet and including a distal-most portion extending along the rotational axis to define the fluid pathway;
a rotor stage positioned at the leading portion, the rotor stage having at least one impeller blade configured to drive a circumferential component and an axial component of a flow into an intermediate pathway portion of the fluid pathway surrounding the intermediate portion; and
a stator stage comprising at least one stator blade extending radially inward from the stator housing in the intermediate pathway portion and defining a gap between the at least one stator blade and the rotor hub, the stator stage configured to reduce the circumferential component of the flow;
an axial dimension of the intermediate portion being greater than a diameter of the intermediate portion; and the flow from the inlet to the outlet being driven primarily by the rotor stage positioned at the leading portion.

14. The blood pump of claim 13, wherein an axial dimension of each of the at least one impeller blade of the rotor stage is greater than the diameter of the intermediate portion.

15. A blood pump configured to provide continuous fluid flow, comprising:
a stator housing having an inlet and an outlet;
a generally cylindrical rotor hub disposed within the stator housing, the rotor hub defining a rotational axis extending from the inlet to the outlet and comprising a body having a leading portion positioned adjacent the inlet, a trailing portion positioned adjacent the outlet, and an intermediate portion between the leading portion and the trailing portion, the leading portion and the trailing portion each exhibit a generally conical geometry;
a fluid pathway of the pump extends from the inlet to the outlet along the rotor hub;
an inlet stator blade extending radially inward from the stator housing within the inlet and including a distal-most portion extending along the rotational axis to define the fluid pathway;
a rotor stage positioned only at the leading portion, the rotor stage having at least one impeller blade configured to drive circumferential and axial components of a flow into an intermediate pathway portion of the fluid pathway surrounding the intermediate portion; and
a stator stage comprising at least one stator blade extending radially inward from the stator housing in the intermediate pathway portion and defining a gap between the at least one stator blade and the rotor hub, the stator stage configured to reduce the circumferential component of the flow;
an axial dimension of the intermediate portion being greater than a diameter of the intermediate portion; and
an axial length of each of the at least one stator blade being less than the diameter of the intermediate portion.

16. The blood pump of claim 15, wherein the rotor hub and the stator housing are configured of blood compatible materials.

17. The blood pump as claimed in claim 15, wherein the stator stage is a first stator stage, further comprising a second stator stage having at least one stator blade extending radially inward from the stator housing in a trailing pathway portion of the fluid pathway surrounding the trailing portion, the second stator stage configured to reduce a circumferential component of the flow.

18. The blood pump as claimed in claim 17, wherein the second stator stage is configured to reduce a circumferential component of the flow within the fluid pathway received from the first stator stage.

19. The blood pump as claimed in claim 17, wherein a portion of the stator housing adjacent the trailing portion decreases in diameter with proximity to the outlet.

20. The blood pump of claim 15, wherein the rotor hub is configured to be magnetically suspended and rotated by stator during operation of the pump.

* * * * *